United States Patent [19]
Hagans et al.

[11] Patent Number: 6,107,509
[45] Date of Patent: Aug. 22, 2000

[54] PROCESS FOR THE RECOVERY OF ACRYLONITRILE AND METHACRYLONTRILE

[75] Inventors: Michael Keith Hagans, Lima; Sanjay Purushottam Godbole, Solon; Patrick Michael Conrath; Donald Eugene Meihls, both of Lima, all of Ohio

[73] Assignee: The Standard Oil Company, Chicago, Ill.

[21] Appl. No.: 09/282,877

[22] Filed: Mar. 31, 1999

[51] Int. Cl.$^7$ .................................................. C07C 255/00
[52] U.S. Cl. ........................................... 558/320; 558/466
[58] Field of Search ...................................... 558/320, 466

[56] References Cited

U.S. PATENT DOCUMENTS 4,166,008   8/1979   Wu et al. ................................ 558/320

*Primary Examiner*—Joseph McKane
*Assistant Examiner*—Joseph Murray
*Attorney, Agent, or Firm*—Thomas E. Nemo; Stephen L. Hensley

[57] ABSTRACT

The process of manufacturing an unsaturated mononitrile selected from the group consisting of acrylonitrile and methacrylonitrile comprising transporting a reactor effluent containing the unsaturated mononitrile to a first column where the reactor effluent is cooled with at least one aqueous stream, transporting the cooled effluent containing the unsaturated mononitrile into a second column where the cooled effluent is contacted with at least one second aqueous stream to absorb the unsaturated mononitrile into at least one second aqueous stream, transporting the second aqueous stream containing the unsaturated mononitrile from the second column to a first distillation column for separation of the crude unsaturated mononitrile from the second aqueous stream, and transporting the separated crude unsaturated mononitrile to a second distillation column to remove at least some impurities from the crude mononitrile, and transporting the partially purified crude unsaturated mononitrile to a third distillation column (product column) to further purified the crude unsaturated mononitrile, recovering the purified unsaturated mononitrile as a sidestream from the product column, introducing about 100 to about 2000 ppm of water in the form consisting of steam and distilled water into the bottom stream obtained from the product column and recycling at least part of the product bottom stream obtained from the product column to the bottom portion of the product column. In another aspect of the present invention the steam and distilled water is added directly to the product column.

18 Claims, 1 Drawing Sheet

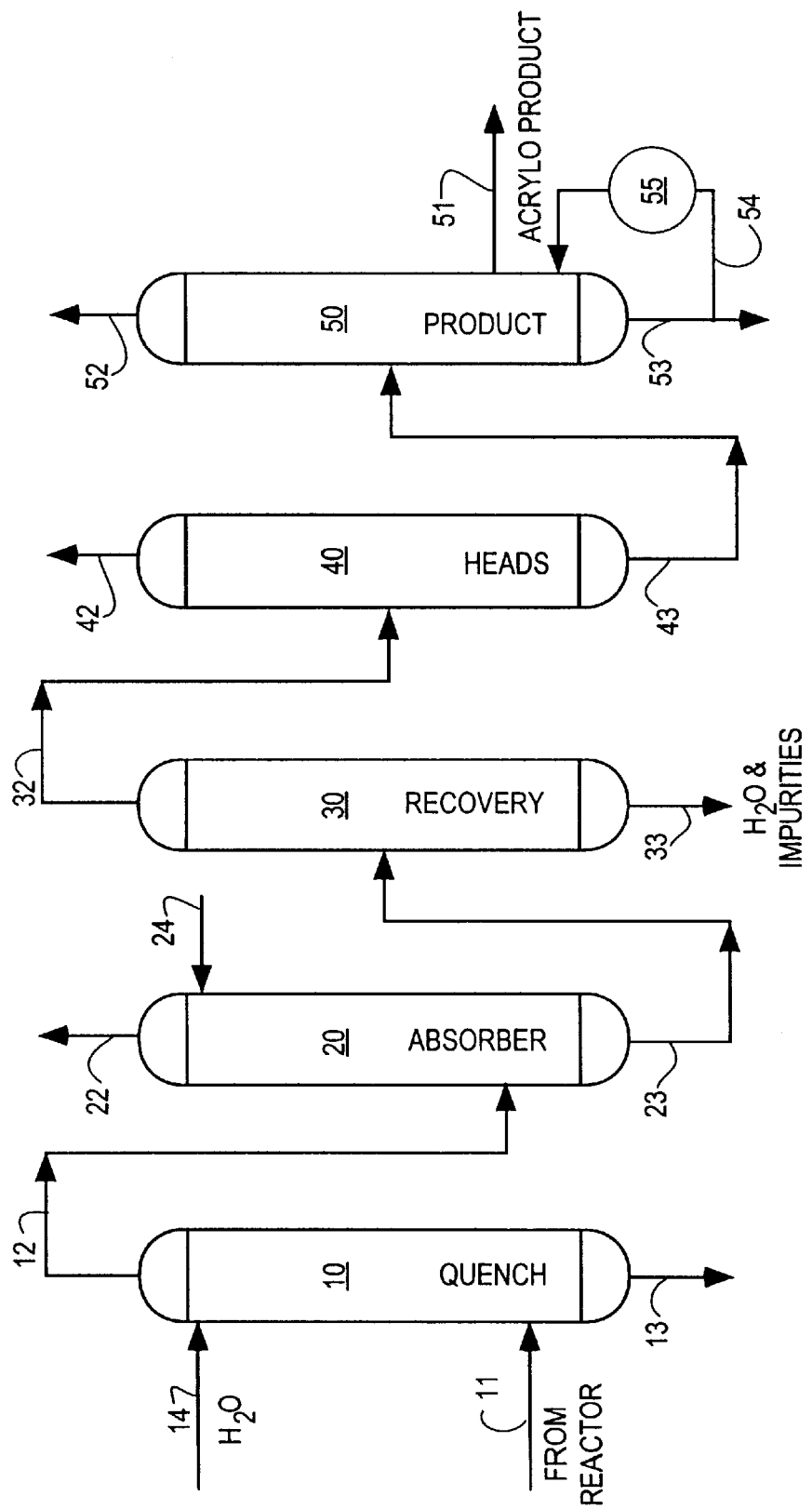

PROCESS FOR THE RECOVERY OF ACRYLONITRILE AND METHACRYLONTRILE

BACKGROUND OF THE INVENTION

The present invention is directed to an improved process for the manufacture of acrylonitrile or methacrylonitrile. In particular, the present invention is directed to an improved process related to the recovery and purification of acrylonitrile or methacrylonitrile produced by the direct reaction of propylene, propane or isobutylene, ammonia and oxygen in the presence of a catalyst.

Typically, recovery and purification of acrylonitrile/methacrylonitrile produced by the direct reaction of a hydrocarbon selected from the group consisting of propane, propylene or isobutylene, ammonia and oxygen in the presence of a catalyst has been accomplished by transporting the reactor effluent containing acrylonitrile/methacrylonitrile to a first column (quench) where the reactor effluent is cooled with a first aqueous stream, transporting the cooled effluent containing acrylonitrile/methacrylonitrile into a second column (absorber) where the cooled effluent is contacted with a second aqueous stream to absorb the acrylonitrile/methacrylonitrile into the second aqueous stream, transporting the second aqueous stream containing the acrylonitrile/methacrylonitrile from the second column to a first distillation column (recovery column) for separation of the crude acrylonitrile/methacrylonitrile from the second aqueous stream, and transporting the separated crude acrylonitrile/methacrylonitrile to a second distillation column (heads column) to remove at least some impurities from the crude acrylonitrile/ methacrylonitrile, and transporting the partially purified acrylonitrile/methacrylonitrile to a third distillation column (product column) to obtain product acrylonitrile/methacrylonitrile. U.S. Pat. Nos. 4,234,510; 3,885,928; 3,352,764; 3,198,750 and 3,044,966 are illustrative of typical recovery and purification processes for acrylonitrile and methacrylonitrile.

Some modifications to the typical recovery and purification process described above have been explored including recycle of the product column bottom stream into the lower portion of the product column via a reboiler. The reboiler is used to reheat the product column bottom stream prior to reentry into the product column. Water addition to the product column including reboiler has been suggested with an attendant observations that corrosion has been a problem in the reboiler tubes.

While the manufacture of acrylonitrile/methacrylonitrile including the recovery and purification have been commercially practiced for years their are still areas in which improvement would have a substantial benefit. One of those areas for improvement is in the substantial elimination or reduction of undesirable polymeric reactions which results in fouling of certain columns over time resulting in the necessity of shut down of the plant for cleaning. The present invention is directed to an improvement in the current acrylonitrile manufacturing process which results in a substantial elimination of fouling in the product column operation thereby substantially increasing the time between shutdowns and cleaning of the plant resulting in a substantial economic benefit during the manufacture of acrylonitrile/methacrylonitrile.

SUMMARY OF THE INVENTION

It is the primary object of the present invention to provide an improved process for the manufacture of acrylonitrile/methacrylonitrile.

It is another object of the present invention to provide an improved process for the recovery and operation of acrylonitrile or methacrylonitrile produced by the direct reaction of a hydrocarbon selected from the group consisting of propylene, propane and isobutylene, ammonia and oxygen in the presence of a catalyst.

Additional objects, advantages and novel features of the invention will be set forth in part in the description which follows, and in part, will become apparent to those skilled in the art upon examination of the following or may be learned by the practice of the invention. The objects and advantages of the invention may be realized and obtained by means of the instrumentalities and combinations particularly pointed out in the appended claims. To achieve the foregoing and other objects and in accordance with the purpose of the present invention as embodied and broadly described herein, the process of the present invention comprises transporting a reactor effluent containing acrylonitrile/methacrylonitrile to a first column (quench) where the reactor effluent is cooled with at least one aqueous stream, transporting the cooled effluent containing acrylonitrile/methacrylonitrile into a second column (absorber) where the cooled effluent is contacted with at least one second aqueous stream to absorb the acrylonitrile/methacrylonitrile into at least one second aqueous stream, transporting at least one second aqueous stream containing the acrylonitrile/methacrylonitrile from the second column to a first distillation column (recovery column) for separation of the crude acrylonitrile/methacrylonitrile from the at least one second aqueous stream, and transporting the separated crude acrylonitrile/methacrylonitrile to a second distillation column (heads column) to remove at least some impurities from the crude acrylonitrile/ methacrylonitrile, and transporting the partially purified acrylonitrile/methacrylonitrile to a third distillation column (product column) to further purified the acrylonitrile/methacrylonitrile, recovering the purified acrylonitrile/methacrylonitrile as a sidestream from the product column, introducing about 100 to about 2000 ppm water in the form consisting of steam and distilled water into a bottom stream obtained from the product column and recycling at least part of the product bottom stream obtained from the product column to the bottom portion of the product column.

In a preferred embodiment of the present invention, the product column bottom stream is recycled to the product column via a product column reboiler.

In a further preferred embodiment of the present invention, the steam or distilled water is added to the product column bottom stream prior to entry into the product column reboiler.

In a still further preferred embodiment of the present invention the steam or distilled water is added to the product column bottom stream in the product column reboiler.

In another preferred embodiment of the present invention the steam or distilled water is added to the product bottom column below the point where the product acrylonitrile is withdrawn from the product column.

In another preferred embodiment of the present invention the steam or distilled water is added to the product bottom column stream after the product bottom column stream has exited the reboiler.

In still another preferred embodiment of the present invention, the process is performed with the reactor effluent obtained from the ammoxidation of propane or propylene, ammonia and oxygen to produce acrylonitrile.

In a further preferred embodiment of the present invention, the reactor effluent is obtained by the reaction of propane, propylene, ammonia and air in a fluid bed reactor while in contact with a fluid bed catalyst.

In another aspect of the present invention, the process comprises transporting a reactor effluent containing acrylonitrile/methacrylonitrile to a first column (quench) where the reactor effluent is cooled with at least one aqueous stream, transporting the cooled effluent containing acrylonitrile/methacrylonitrile into a second column (absorber) where the cooled effluent is contacted with at least one second aqueous stream to absorb the acrylonitrile/methacrylonitrile into at least one second aqueous stream, transporting at least one second aqueous stream containing the acrylonitrile/methacrylonitrile from the second column to a first distillation column (recovery column) for separation of the crude acrylonitrile/methacrylonitrile from the at least one second aqueous stream, and transporting the separated crude acrylonitrile/methacrylonitrile to a second distillation column (heads column) to remove at least some impurities from the crude acrylonitrile/ methacrylonitrile, and transporting the partially purified acrylonitrile/methacrylonitrile to a third distillation column (product column) to further purified the acrylonitrile/methacrylonitrile, recovering a sidestream containing the purified acrylonitrile/methacrylonitrile from the product column, recycling at least part of the product bottom stream obtained from the product column to the bottom portion of the product column and introducing directly into the product column below the point where the sidestream containing acrylonitrile/methacrylonitrile is located about 100 to about 2000 ppm water in the form consisting of steam and distilled water.

In a further aspect of the present invention, the process for the manufacture of an unsaturated mononitrile selected from the group consisting of acrylonitrile and methacrylonitrile comprises reacting a hydrocarbon selected from the group consisting of propane, propylene and isobutylene with ammonia and oxygen in a reaction zone in the presence of a catalyst to produce the corresponding mononitrile, recovering the corresponding mononitrile from the reaction zone, distilling the recovered mononitrile in a series of distillation columns to remove substantially all of the impurities from the mononitrile, recovering the purified mononitrile as a sidestream from the final distillation column and directly introducing about 100 to about 2000 ppm of water in the form selected from the group consisting of steam, distilled water and mixtures thereof into the final distillation column at a point in the final distillation column below which the sidestream containing purified mononitrile is located.

In still another aspect of the present invention, he process for the manufacture of an unsaturated mononitrile selected from the group consisting of acrylonitrile and methacrylonitrile comprises reacting a hydrocarbon selected from the group consisting of propane, propylene and isobutylene with ammonia and oxygen in a reaction zone in the presence of a catalyst to produce the corresponding mononitrile, recovering the corresponding mononitrile from the reaction zone, distilling the recovered mononitrile in a series of distillation columns to remove substantially all of the impurities from the mononitrile, recovering the mononitrile as a sidestream from the final distillation column, introducing about 100 to about 2000 ppm of water in the form selected from the group consisting of steam, distilled water and mixtures thereof into a bottom stream obtained from the final distillation column and recycling at least part of the bottom stream obtained from the final distillation column to the bottom portion of the final distillation column.

It has been found that the injection of steam or distilled water into the product column bottom stream in the amounts set forth above has led to a substantial minimization in the formation of polymeric deposit the product column and the reboiler. The result of this substantial reduction in unwanted polymeric reactions is an increase in run time between planned plant maintenance. In the practice of the present invention applicants have been able to increase the run time between product column reboiler maintenance at least by six fold and no detectable polymerization in the product column which results in significant economical savings without any observation of corrosion problems.

Conventional fluid bed ammoxidation catalyst may be utilized in the practice of the invention. For example, fluid bed catalyst as described in U.S. Pat. Nos. 3,642,930 and 5,093,299, herein incorporated by reference, may be utilized in the practice of the present invention.

BRIEF DESCRIPTION OF THE DRAWING

FIG. 1 is a schematic representation of the process of the present invention applied to the manufacture of acrylonitrile

DETAILED DESCRIPTION OF THE INVENTION

The process of the present invention will now be described in detail with reference to FIG. 1.

The reactor effluent obtained by the direct reaction of propane or propylene, ammonia and oxygen containing gas in a reaction zone (not shown) in the presence of a catalyst is transported to a quench column 10 via conduit 11, wherein the hot reactor effluent gases are cooled by contact with an aqueous stream entering column 10 via line 14. The cooled effluent gas comprising acrylonitrile (including coproducts such as acetonitrile, hydrogen cyanide and impurities) is then passed into the bottom of an absorber column 20 via line 12 wherein the acrylonitrile is absorbed in a second aqueous stream which enters the top of absorber column 20 via line 24. The non-absorbed effluent exits from the top of absorber column 20 through pipe 22. The aqueous stream containing the acrylonitrile is then transported from the absorber 20 via line 23 to the upper portion of a first distillation column 30 (recovery column) for further product purification. The partially purified acrylonitrile product is recovered from the top portion of recovery column 30 and sent to a second distillation column 40 (heads column) 40 via line 32, while water and other impurities are removed from the recovery column 30 via line 33. In the heads column 40, coproducts such as the HCN may be separated and removed from the acrylonitrile in an overhead stream via line 42. The acrylonitrile containing stream is then transferred to a third distillation column (product column) 50 for further purification. Purified acrylonitrile is removed from product column 50 as a sidestream via line 51. The bottom stream exits the product column 50 via line 53. At least a portion of this bottom product stream is recycled into product column 50 via line 54. This recycled bottom product stream enters a reboiler 55 where it is reheated prior to recycle into product column 50. In addition, in accordance with the practice of the present invention the recycled bottom product stream is treated with steam or distilled water so that this stream contains between about 100 to 2000 ppm of water prior to reentry into the product column 50. Although it is believed that the steam or distilled water may be injected into the recycled bottom product stream at any point prior to reentry into the product column bottoms and reboiler loop it is preferred to inject the steam or distilled water into the recycled product bottom stream prior to entry into reboiler 55.

In a preferred embodiment of the present invention, steam or distilled water in the range of 500 to 1000 ppm is injected into the product bottom stream.

Preferably, the ammoxidation reaction is performed in a fluid bed reactor although other types of reactors such as transport line reactors are envisioned.

Fluid bed reactors, for the manufacture of acrylonitrile are well known in the prior art. For example, the reactor design set forth in U.S. Pat. No. 3,230,246, herein incorporated by reference, is suitable.

Conditions for the ammoxidation reaction to occur are also well known in the prior art as evidenced by U.S. Pat. Nos. 5,093,299; 4,863,891; 4,767,878 and 4,503,001; herein incorporated by reference. Typically, the ammoxidation process is performed by contacting propane, propylene or isobutylene in the presence of ammonia and oxygen with a fluid bed catalyst at an elevated temperature to produce the acrylonitrile or methacrylonitrile. Any source of oxygen may be employed. For economic reasons, however, it is preferred to use air. The typical molar ratio of the oxygen to olefin in the feed should range from 0.5:1 to 4:1, preferably from 1:1 to 3:1. The molar ratio of ammonia to olefin in the feed in the reaction may vary from between 0.5:1 to 5:1. There is really no upper limit for the ammonia-olefin ratio, but there is generally no reason to exceed a ratio of 5:1 for economic reasons.

The reaction is carried out at a temperature of between the ranges of about 260° to 600° C., but the preferred ranges being 310° to 500° C., especially preferred being 350° to 480° C. The contact time, although not critical, is generally in the range of 0.1 to 50 seconds, with preference being to a contact time of 1 to 15 seconds.

Any conventional fluid bed ammoxidation catalyst may be utilized in the practice of the present invention. Specific examples of suitable ammoxidation catalyst can be found in U.S. Pat. Nos. 3,642,930; 5,093,299, and 5,854,172 herein incorporated by reference.

Typically, the absorber column, recovery column and heads column, product column are maintained in the range between 0 to 15 psig, and 0 to 20 psig, 0 to 10 psig, and −12 to 1 psig, respectively.

As will be evident to those skilled in the art, various modifications of this invention can be made or followed in light of the foregoing disclosure and discussion without departing from the spirit and scope of the disclosure or from the scope of the claims.

What we claim as our invention is:

1. A process for the manufacture of an unsaturated mononitrile selected from the group consisting of acrylonitrile and methacrylonitrile comprising transporting a reactor effluent containing the unsaturated mononitrile to a first column where the reactor effluent is cooled with a first aqueous stream, transporting the cooled effluent containing the unsaturated mononitrile into a second column where the cooled effluent is contacted with a second aqueous stream to absorb the unsaturated mononitrile into the second aqueous stream, transporting the second aqueous stream containing the unsaturated mononitrile from the second column to a first distillation column for separation of the crude unsaturated mononitrile from the second aqueous stream, and transporting the separated crude unsaturated mononitrile to a second distillation column to remove at least some impurities from the crude mononitrile, and transporting the partially purified crude unsaturated mononitrile to a third distillation column to further purify the crude unsaturated mononitrile, recovering the purified unsaturated mononitrile in a sidestream from the third distillation column, introducing about 100 to about 2000 ppm of water in the form selected from the group consisting of steam, distilled water and mixtures thereof into the bottom stream obtained from the third distillation column and recycling at least part of the bottom stream obtained from the third distillation column to the bottom portion of the third distillation column.

2. The process of claim 1 wherein the water in the form selected from the group consisting of steam, distilled water and mixtures thereof is introduced into the bottom stream in the range of 500 to 1000 ppm.

3. The process of claim 1 comprising recycling the bottom stream to the third distillation column through a reboiler.

4. The process of claim 3 wherein the water in the form selected from the group consisting of steam, distilled water and mixtures thereof is added to the bottom stream prior to entry into the reboiler.

5. The process of claim 3 wherein the water in the form selected from the group consisting of steam, distilled water and mixtures thereof is added directly into the reboiler.

6. The process of claim 3 wherein the water in the form selected from the group consisting of steam, distilled water and mixtures thereof is added to the bottom stream after the bottom column stream has exited the reboiler.

7. The process of claim 1 wherein the gaseous reactor effluent is obtained from the ammoxidation of a hydrocarbon selected from the group consisting of propane and propylene, ammonia and oxygen to produce acrylonitrile.

8. The process of claim 1 wherein the gaseous reactor effluent is obtained by the reaction of a hydrocarbon selected from the group consisting of propane and propylene, ammonia and air in a fluid bed reactor while in contact with a fluid bed catalyst.

9. The process of claim 1 wherein the gaseous reactor effluent is obtained from the ammoxidation of isobutylene, ammonia and oxygen to produce methacrylonitrile.

10. The process of claim 1 wherein the gaseous reactor effluent is obtained by the reaction of isobutylene, ammonia and air in a fluid bed reactor while in contact with a fluid bed catalyst.

11. The process for the manufacture of an unsaturated mononitrile selected from the group consisting of acrylonitrile and methacrylonitrile comprising transporting a reactor effluent containing the unsaturated mononitrile to a first column where the reactor effluent is cooled with a first aqueous stream, transporting the cooled effluent containing mononitrile into a second column where the cooled effluent is contacted with a second aqueous stream to absorb the mononitrile into the second aqueous stream, transporting the second aqueous stream containing the mononitrile from the second column to a first distillation column for separation of the crude mononitrile from the second aqueous stream, and transporting the separated crude mononitrile to a second distillation column to remove at least some impurities from the crude mononitrile, and transporting the partially purified mononitrile to a third distillation column to further purify the mononitrile, recovering a sidestream containing the purified mononitrile from the third distillation column, recycling at least part of the bottom stream obtained from the third distillation column to the bottom portion of the third distillation column and introducing about 100 to about 2000 ppm water in the form selected from the group consisting of steam, distilled water and mixtures thereof directly into the third distillation column below the point where the sidestream containing mononitrile is located about 100 to about 2000 ppm water.

12. The process of claim 11 wherein the water in the form selected from the group consisting of steam, distilled water and mixtures thereof is introduced in the range of 500 to 1000 ppm.

13. The process of claim 11 wherein the gaseous reactor effluent is obtained from the ammoxidation of a hydrocarbon selected from the group consisting of propane and propylene, ammonia and oxygen to produce acrylonitrile.

14. The process of claim 13 wherein the gaseous reactor effluent is obtained by the reaction of a hydrocarbon selected from the group consisting of propane and propylene, ammonia and air in a fluid bed reactor while in contact with a fluid bed catalyst.

15. The process of claim 11 wherein the gaseous reactor effluent is obtained from the ammoxidation of isobutylene, ammonia and oxygen to produce methacrylonitrile.

16. The process of claim 15 wherein the gaseous reactor effluent is obtained by the reaction of isobutylene, ammonia and air in a fluid bed reactor while in contact with a fluid bed catalyst.

17. The process for the manufacture of an unsaturated mononitrile selected from the group consisting of acrylonitrile and methacrylonitrile comprising reacting a hydrocarbon selected from the group consisting of propane, propylene and isobutylene with ammonia and oxygen in a reaction zone in the presence of a catalyst to produce the corresponding mononitrile, recovering the corresponding mononitrile from the reaction zone, distilling the recovered mononitrile in a series of distillation columns to remove substantially all of the impurities from the mononitrile, recovering the puritied mononitrile as a sidestream from the final distillation column and directly introducing about 100 to about 2000 ppm of water in the form selected from the group consisting of steam, distilled water and mixtures thereof into the final distillation column at a point in the final distillation column below which the sidestream containing purified mononitrile is located.

18. The process for the manufacture of an unsaturated mononitrile selected from the group consisting of acrylonitrile and methacrylonitrile comprising reacting a hydrocarbon selected from the group consisting of propane, propylene and isobutylene with ammonia and oxygen in a reaction zone in the presence of a catalyst to produce the corresponding mononitrile, recovering the corresponding mononitrile from the reaction zone, distilling the recovered mononitrile in a series of distillation columns to remove substantially all of the impurities from the mononitrile, recovering the purified mononitrile as a sidestream from the final distillation column, introducing about 100 to about 2000 ppm of water in the form selected from the group consisting of steam, distilled water and mixtures thereof into a bottom stream obtained from the final distillation column and recycling at least part of the bottom stream obtained from the final distillation column to the bottom portion of the final distillation column.

* * * * *